(12) United States Patent
Wakamatsu et al.

(10) Patent No.: US 7,552,639 B2
(45) Date of Patent: Jun. 30, 2009

(54) QUARTZ SENSOR AND SENSING DEVICE

(75) Inventors: Shunichi Wakamatsu, Sayama (JP); Mitsuaki Koyama, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 0 days.

(21) Appl. No.: 11/792,964

(22) PCT Filed: Dec. 14, 2005

(86) PCT No.: PCT/JP2005/023417

§ 371 (c)(1),
(2), (4) Date: Sep. 10, 2007

(87) PCT Pub. No.: WO2006/064951

PCT Pub. Date: Jun. 22, 2006

(65) Prior Publication Data
US 2008/0047331 A1 Feb. 28, 2008

(30) Foreign Application Priority Data
Dec. 15, 2004 (JP) ............................. 2004-363512

(51) Int. Cl.
G01N 29/00 (2006.01)
(52) U.S. Cl. ................. 73/579; 73/54.24; 73/54.41
(58) Field of Classification Search ............. 73/579, 73/54.41, 54.24, 54.25, 61.79
See application file for complete search history.

(56) References Cited
U.S. PATENT DOCUMENTS
4,991,283 A 2/1991 Johnson et al.

(Continued)

FOREIGN PATENT DOCUMENTS
JP 1-244335 9/1989

(Continued)

OTHER PUBLICATIONS
U.S. Appl. No. 11/989,884, filed Jan. 31, 2008, Takeo Oita, et al.

Primary Examiner—Hezron Williams
Assistant Examiner—J M Saint Surin
(74) Attorney, Agent, or Firm—Jordan and Hamburg LLP

(57) ABSTRACT

An object of the present invention is to provide a highly sensitive Langevin type quartz sensor which is easy in assembling, is less likely to cause damage to a quartz resonator during the assembly work, and is easy to perform a measurement work. As a specific means to solve the problem, a recess is formed in a quartz holding member made of, for instance, rubber, and an airtight space is formed by holding the quartz resonator with the quartz holding member so as to cover the recess. In the meantime, a hole is provided in a circuit board and a projected portion which projects toward back side of the recess in the quartz holding member is fitted into this hole. Then, a resonator electrode of the quartz resonator and an electrode of the circuit board are electrically connected using a conductive adhesive, a pouring space for a sample solution is formed by pressing a position surrounding the quartz resonator in the quartz holding member toward the circuit board side with a lid so that the quartz sensor is structured. Since there is no possibility for such a quartz sensor that the quartz resonator is directly pressed and an excessive force is applied to the quartz resonator during manufacturing and the quartz resonator is not in direct contact with the circuit board, damage to the quartz resonator is suppressed.

12 Claims, 10 Drawing Sheets

U.S. PATENT DOCUMENTS

| | | | |
|---|---|---|---|
| 5,196,347 A * | 3/1993 | Kaneko et al. | 436/127 |
| 5,494,639 A | 2/1996 | Grzegorzewski | |
| 5,892,143 A | 4/1999 | Namerikawa et al. | |
| 6,210,226 B1 * | 4/2001 | Zhu et al. | 439/607 |
| 6,321,588 B1 | 11/2001 | Bowers et al. | |
| 6,525,549 B1 | 2/2003 | Poellmann | |
| 6,938,462 B2 | 9/2005 | Jakoby et al. | |
| 7,046,096 B2 | 5/2006 | Kobayashi | |
| 7,055,377 B2 * | 6/2006 | Paul et al. | 73/54.41 |
| 2004/0016297 A1 | 1/2004 | Paul et al. | |
| 2004/0187580 A1 | 9/2004 | Nozaki | |
| 2005/0052813 A1 | 3/2005 | Kobayashi | |
| 2006/0141608 A1 | 6/2006 | Aastrup et al. | |
| 2008/0047331 A1 | 2/2008 | Wakamatsu et al. | |
| 2008/0129148 A1 * | 6/2008 | Wakamatsu et al. | 310/319 |
| 2008/0134767 A1 * | 6/2008 | Wakamatsu et al. | 73/61.79 |
| 2008/0156097 A1 * | 7/2008 | Onishi et al. | 73/579 |

FOREIGN PATENT DOCUMENTS

| | | |
|---|---|---|
| JP | 3-188350 | 8/1991 |
| JP | 3-257346 | 11/1991 |
| JP | 4-1554 | 1/1992 |
| JP | 4-9744 | 1/1992 |
| JP | 5-5735 | 1/1993 |
| JP | 7-190916 | 7/1995 |
| JP | 7-190919 | 7/1995 |
| JP | 9-145583 | 6/1997 |
| JP | 9-250936 | 9/1997 |
| JP | 10-038788 | 2/1998 |
| JP | 10-142134 | 5/1998 |
| JP | 10-332463 | 12/1998 |
| JP | 11-183479 | 7/1999 |
| JP | 2000-338022 | 12/2000 |
| JP | 2001-83154 | 3/2001 |
| JP | 2001-099777 | 4/2001 |
| JP | 2001-201436 | 7/2001 |
| JP | 2002-148295 | 5/2002 |
| JP | 2002-243607 | 8/2002 |
| JP | 2004-506194 | 2/2004 |
| JP | 2004-205392 | 7/2004 |
| JP | 2004-264254 | 9/2004 |
| JP | 2005-43123 | 2/2005 |

* cited by examiner

QUARTZ SENSOR AND SENSING DEVICE

TECHNICAL FIELD

The present inventor relates to a quartz sensor utilizing a Langevin type quartz resonator which is composed such that one surface of a quartz piece comes in contact with a measurement medium and the other surface faces an airtight space to sense an object to be detected by detecting variation in frequency, and to a sensing device using the quartz sensor.

BACKGROUND ART

A measuring method that uses a sensing device equipped with a quartz sensor using a quartz resonator for sensing a substance in minute quantities such as an environmental pollutant e.g. dioxine or the like, or a disease marker for the hepatitis C virus, a C-reactive protein (CRP), or the like has been widely known.

To be more specific, the measurement method is conducted in such a manner that an adsorbing layer is formed in advance on an excitation electrode on one surface side of the quartz resonator, and the presence/absence of the object to be measured or the concentration thereof in a sample solution is measured by applying a property that when the object is adsorbed, the resonance frequency of the quartz piece varies according to the mass of the adsorbed substance. In Patent Document 1, there is a description that for the purpose that the quartz resonator equipped in the quartz sensor used in this measurement method be oscillated in a stable fashion in an immuno-latex solution, it is desirable to have a structure in which only one surface of the quartz resonator comes in contact with a measurement medium.

Such a quartz sensor is usually called a Langevin type quartz resonator. Though not described in Patent Document 1, the fundamental structure of the Langevin type quartz resonator generally has a composition shown in FIG. 10. 10 in the drawing is a round quartz piece, and foil-shaped electrodes 11 and 12 are respectively formed at the center of both surfaces. Supporting line members 13 and 14 to take out an electric signal outside, lead wires of, for instance about 0.5 mm in diameter are connected to these electrodes 11 and 12. A base 16 having a recess 15 is placed on the other surface side of the quartz piece 10. The quartz piece 10 and the base 16 are adhered firmly by an adhesive 17, thereby forming an airtight space enclosed by the quartz piece 10 and the recess 15.

In recent years, further control of toxic substances which have a large effect on an environment such as the above-described dioxin or the like that has been demanded from the viewpoint of environmental protection, and attempts to achieve measurement in the ppt level have been widely conducted. In a quartz resonator, the resonance frequency of the quartz resonator increases as the thickness of the quartz piece decreases. From the Sauerbrey equation, the greater the frequency generated by the quartz resonator, the more the amount of deviation in frequency in regard to the amount of change in mass of the object. In other words, when the quartz piece becomes thinner and thinner, the measurement sensitivity of the quartz sensor increases, so that the measurement of a substance in minute quantities becomes possible. Therefore, reduction in the thickness of the quartz piece is required.

The technology to reduce the layer thickness of a quartz piece has progressed at present, and it has become possible to manufacture a quartz piece with a thickness of several to several tens of μm. As for a method of manufacturing a quartz sensor as shown in FIG. 10, a method in which a quartz resonator is sandwiched with, for instance, two plastic cases having a specific shape in a manner that an airtight space is formed between one surface of the quartz resonator and the plastics, so that the quartz resonator is fixed in the plastic cases by welding the plastic cases together by ultrasonic waves has been attempted. When such a method is used, however, the thin layered quartz piece is in danger of being damaged by the vibration due to the ultrasonic waves. It is also conceivable to adopt injection molding, but injection molding has the disadvantage of complicating the manufacturing process.

In Patent Document 2, there is a description of a structure prepared in such that a rectangular notch a little smaller than the quartz resonator is formed at the center of one side of a square flexible substrate, the quartz resonator is attached to the flexible substrate so that the quartz resonator is caught in the notch, and the flexible substrate, a high polymer elastic sheet, and a holding substrate are united by screwing them together. When taking this structure, it is possible to manufacture a quartz sensor without application of ultrasonic waves as described in the above method of manufacturing.

However, it is understood from the exploded perspective view of the quartz sensor in Patent Document 2 that it is structured in a manner that the periphery of the quartz resonator is sandwiched between the high polymer elastic sheet and the flexible substrate, and a strong force is applied on the periphery of the quartz resonator when the screw is fastened to ensure the airtightness. Accordingly, the possibility of damaged during the manufacturing process is much larger when the thickness of the quartz resonator is reduced.

In addition, though the quartz sensor functions as the detector in a sensing device by being connected to a measurement device main unit, which performs signal processings, when the quartz sensor is connected to the measurement device main unit, a special attachment is required in the method in Patent Documents 1 and 2. When measuring, for instance, 8 samples which are different in dilution ratio, are prepared from the same sample to be measured, and measurement for each sample is performed so as to increase the measurement accuracy. At this time, there is a disadvantage that the measurement work is troublesome because the wiring for the respective samples spread over a work bench which is used at the time of the measurement.

Patent Document 1: Japanese Patent Application Laid-open No. 2001-83154 (paragraph 0009, column 0019 and FIG. 1)

Patent Document 2: Japanese Patent Application Laid-open No. Hei 11-183479 (paragraph 0024, FIG. 2 and FIG. 9)

DISCLOSURE OF THE INVENTION

The problem of the present invention is to resolve the above-described disadvantages of the conventional technology, and an object of the present invention is to provide a Langevin type quartz sensor which can be easily assembled and reduces damage to the quartz resonator during operation, and a sensing device thereof. Another object of the present invention is to provide a Langevin type quartz sensor and a sensing device using the same which are easy of measurement A quartz sensor of the present invention used for detecting an object to be measured in a sample solution, comprising:

a circuit board equipped with a connecting terminal unit which is connected to a measuring device main unit and an electrode electrically connected to the connecting terminal unit;

a quartz holding member made from an elastic material provided with a recess for forming an airtight space, and stacked above the above-described circuit board;

a quartz resonator equipped with excitation electrodes which are arranged on one surface side and on the other surface side of a quartz piece respectively and electrically connected to the electrodes of the above-described circuit board, and held by the above-described quartz holding member in a state that the excitation electrode on the other surface side covers the recess so as to face the above-described recess;

an adsorbing layer provided on the excitation electrode on the above-described one surface side, and for adsorbing the object to be measured in the sample solution;

a lid closely contacting with the periphery of the above-described recess in the quartz holding member, and forming a pouring space for the sample solution by enclosing the upper space on one surface side of the quartz resonator; and a conductive adhesive to stick the excitation electrode of the quartz resonator and the electrode of the circuit board, wherein the natural frequency of the quartz resonator varies by adsorption of the object to be measured on said adsorbing layer.

The quartz sensor can be structured such that in the above-described quartz holding member, a hole for the conductive adhesive is formed at a position corresponding to the excitation electrode, and the excitation electrode and the electrode of the circuit board are stuck together by the conductive adhesive via the hole. It can be also structured such that a hole for the quartz holding member is formed in the circuit board, and the bottom side of the recess for the quartz holding member is fitted into the hole from the one surface side of the circuit board. In the above-described quartz sensor, a claw which is bent toward inside is formed on the periphery of the above-described lid, a notch is formed on the above-described circuit board, so that the lid may be fitted on the circuit board by locking the periphery of the circuit board with the claw due to the restoration force of the claw toward inside at the notched portion.

Another quartz sensor relating to the present invention used for detecting an object to be measured in a sample solution, comprising:

a circuit board including a connecting terminal unit connected to a measuring device main unit, an electrode electrically connected to the connecting terminal unit and a hole;

a ring-shaped quartz holding member fitted into said hole and made of an elastic material;

a quartz resonator equipped with excitation electrodes which are arranged on one surface side and on the other surface side of a quartz piece respectively and electrically connected to the electrodes of the above-described circuit board, and held by the above-described quartz holding member so as to cover the above-described ring-shaped quartz holding member on one surface side of the circuit board;

an adsorbing layer provided on the excitation electrode on the above-described one surface side, and for adsorbing the object to be measured in the sample solution;

a base support structured to form an airtight space on the other surface side of the above-described quartz resonator for covering one surface side of the circuit board;

a lid closely contacting with the periphery of a ring hole in the above-described quartz holding member on the other surface side of the circuit board, and forming a pouring space for the sample solution by enclosing an upper space on the other surface side of the quartz resonator so as to cover the other surface side of the circuit board; and a conductive adhesive for bonding the excitation electrode of the above-described quartz resonator and the electrode of the above-described circuit board, wherein the natural frequency of the quartz resonator varies by adsorption of the object to be measured on the adsorbing layer.

Rubber is preferred as the material for the quartz holding member in the quartz sensor. The quartz sensor may include a pouring opening for confirming that the sample solution is poured into the pouring space, and a confirmation opening of the sample solution on the upper surface of the above-described lid, in which the pouring opening and the confirmation opening may be connected in the inside of the lid. In addition, the circuit board may be structured so as to be inserted into and removed from the measuring device main unit, and when it is inserted, the connecting terminal unit may be connected to the measuring device main unit.

The sensing device of the present invention includes the quartz sensor of the above-described present invention, and a measuring device main unit for detecting the variation of the natural frequency of a quartz resonator and detecting the object to be measured in the sample solution based on the detection result.

The quartz sensor of the present invention forms an airtight space by holding the quartz resonator with the quartz holding member so as to cover the recess of the quartz holding member made of, for instance, rubber; the resonator electrode of the quartz resonator and the electrode of the circuit board are electrically connected using the conductive adhesive; and the pouring space of the sample solution is formed by pressing a portion of the quartz holding member surrounding the quartz resonator by the lid toward the circuit board side. Therefore, since the assembling work is easy, and there is no possibility of applying excessive force on the quartz resonator by directly pressing the quartz resonator at the time of manufacturing according to the present invention, for instance, damage to the quartz resonator at the time of, manufacturing is suppressed. Since the circuit board is not in direct contact with the quartz resonator, the degree of receiving external stress is small even if the quartz resonator is made thin. Accordingly, it is possible to perform the measurement with high accuracy even at a high frequency. When the portion of the quartz holding member corresponding to the recess is structured to be inserted into the hole of the circuit board, if a portion protruding downward is formed in response to the recess by reducing the thickness of the quartz holding member, since this portion can be housed in the recess of the circuit board, the thickness of the quartz holding member can be reduced as a result.

Further, a quartz sensor of still another invention ensures the pouring space of the sample solution and the airtight space by fitting a ring-shaped quartz holding member into the hole of the circuit board, installing the quartz resonator in the quartz holding member so as to cover the ring hole, and pressing the lid and the base support from both surfaces of the circuit board. Therefore also in this invention, since the assembling task is easy, and there is no possibility that excessive force is applied on the quartz resonator by pressing the quartz resonator directly at the time of manufacturing, an effect similar to that in the above-described invention can be obtained. Further, in the present invention, since a connecting terminal unit directly connected to a terminal on the measuring device main unit side is installed to the circuit board of the quartz sensor, an attachment or the like to be used at the time of connecting the quartz sensor to the measuring device main unit becomes unnecessary. Accordingly, the measurement work is made easier because the above-described wiring is not routed around on a measurement table.

BEST MODE FOR CARRYING OUT THE INVENTION

First Embodiment

Figure 1:
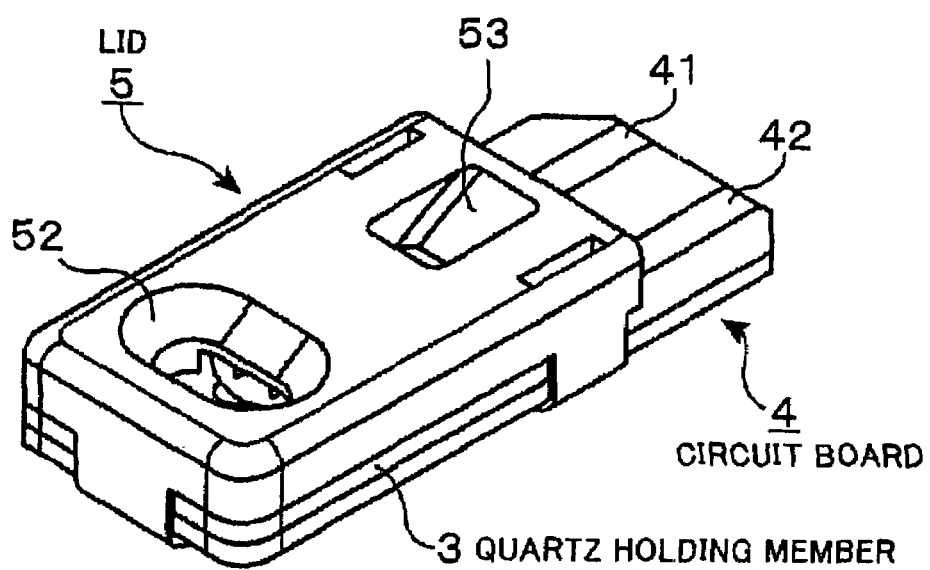
FIG. 1 is a perspective view showing an embodiment of a quartz sensor relating to the present invention.
Figure 2:
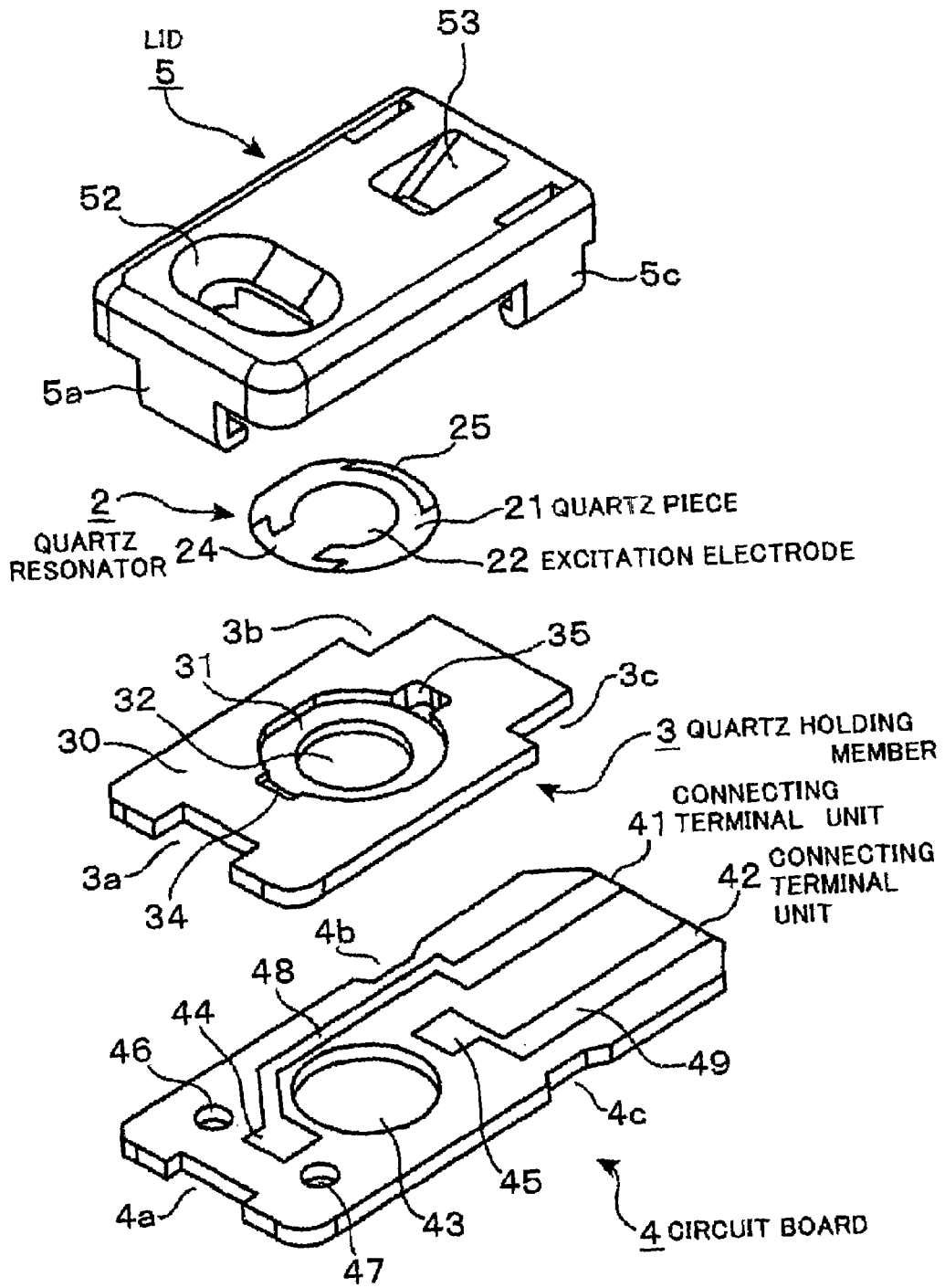
FIG. 2 is an exploded perspective view showing the upper surfaces of respective parts of the quartz sensor.

The first embodiment of the quartz sensor relating to the present invention will be explained using FIG. 1 to FIG. 4. FIG. 1 is a perspective view showing an example of the quartz sensor relating to the present invention. The quartz sensor is structured by placing one upon another composed of the respective parts of a circuit board 4, a quartz holding member 3, a quartz resonator 2 and a lid 5 in this order from the bottom. FIG. 2 is a exploded perspective view showing the upper surface sides of the respective parts of the quartz sensor.

The quartz resonator 2 includes a quartz piece 21, excitation electrodes 22 and 23, and derivation electrodes 24 and 25. The quartz piece 21 has an equivalent thickness of 1 μm to 300 μm, preferably 185 μm, and is formed in a plate in which a portion of the periphery is cut off straight. On one surface side and the other surface side of the quartz piece 21, one foil-shaped excitation electrode 22 and the other foil-shaped excitation electrode 23 are stacked respectively and formed in a disk having a smaller diameter than the quartz piece 21. On one surface side of the quartz piece 21, an end of the foil-shaped derivation electrode 24 is connected to the excitation electrode 22, and the derivation electrode 24 is bent along the edge of the quartz piece 21, and turned back on the other surface side of the quartz piece. These excitation electrodes 22, 23 and the derivation electrodes 24, 25 serve as resonator electrodes.

In addition, on the other surface side of the quartz piece 21, the end of the other foil-shaped derivation electrode 25 is connected to the other excitation electrode 23 in a similar layout to that of the previously described derivation electrode 24, and the layouts of the excitation electrode 22 (23) and the derivation electrode 24 (25) are the same as each other on both surfaces of the quartz piece 21.

The equivalent thickness of the excitation electrodes 21, 22 and the derivation electrodes 23, 24 is, for instance, 0.2 μm, and though gold or silver is suitable for the material for the electrode, gold is more suitable because of high stability of frequency in a fluid, and the resistance against oxidation of the electrode surface during preservation in the air before use. An antibody or the like which is an adsorbing layer that selectively adsorbs an object, for instance dioxin, with the quartz sensor, is stuck on one surface side of the quartz resonator 2 in advance.

The quartz holding member 3 holding the quartz resonator 2 is made of a rubber sheet with a thickness of, for instance, 1 mm, and is formed in a shape matching for the circuit board 4 which will be described later. That is, the quartz holding member 3 is formed in a shape in which a rectangular notch 3a is formed in the center of one end on the front side of a rectangular body, and rectangular notches 3b and 3c are formed respectively at both corners on the rear side. Note that though rubber is preferable for the material for the quartz holding member 3, other elastic material can also be used. A recess 31 is formed on one surface side of the quartz holding member 3 in a form to be a similar figure to the shape of the quartz resonator 2 so that the quartz resonator 2 can be easily placed in the recess 31. As for the size, it is formed in a size substantially similar to the size of the quartz resonator 2, for instance, in a size similar to or a little larger than the quartz resonator 2. At the portion outside of the recess 31, through holes 34 and 35 which serve as spaces for applying a conductive adhesive to be described later are drilled so as to face each other on the outside of the recess 31. It should be noted that the depth of the recess 31 is designed to be a little greater than the thickness of the quartz resonator 2. In the bottom center of the recess 31, a round recess 32 which matches with the size of the excitation electrode 23 and forms an airtight atmosphere coming into contact with the excitation electrode 23 is formed.

The circuit board 4 will be explained next. The circuit board 4 is composed of, for instance, printed circuit boards, and an electrode 44, a hole 43 and an electrode 45 are formed in this order from the front end toward a rear end side. The hole 43 is formed in a circular shape matching with a round projection 33 projecting from the back surface side of the quartz holding member 3. Two conductive path patterns in parallel lines are formed as connecting terminal units 41 and 42 respectively at a little to the rear end side from the position where the electrode 45 is formed. The one connecting terminal unit 41 is electrically connected to the electrode 44 via a pattern 48, and the other connecting terminal unit 42 is electrically connected to the electrode 45 via a pattern 49. Holes 46 and 47 are engaging holes to engage with engaging protrusions 36 and 37 (refer to FIG. 3) of the quartz holding member 3. The quartz holding member 3 is fixed on the circuit board 4 in a state that the front surface of the circuit board 4 and the back surface of the quartz holding member 3 are kept in absolute contact with one another by inserting the projection 33 projecting toward back surface side of the above-described quartz holding member 3 into the hole 43 of the circuit board 4, and at the same time by fitting (engaging) engaging projections 36 and 37 of the quartz holding member 3 into the engaging holes 46 and 47 of the circuit board 4. At this time, a portion of or the whole of the electrodes 44 and 45 are exposed in the upper surface via the holes 34 and 35 of the quartz holding member 3.

Figure 3:
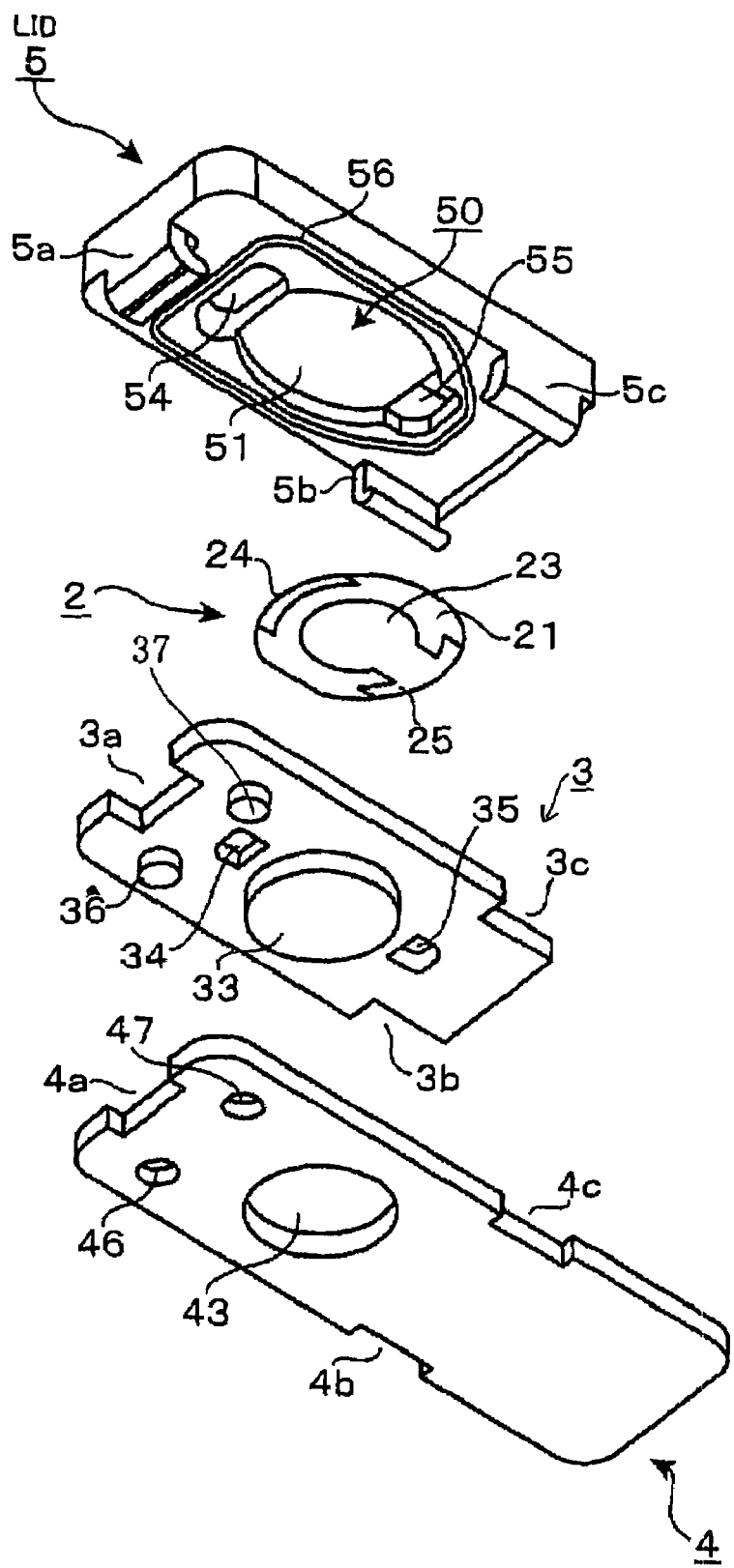
FIG. 3 is an exploded perspective view showing the bottom surfaces of the respective parts of the quartz sensor.
Figure 4:
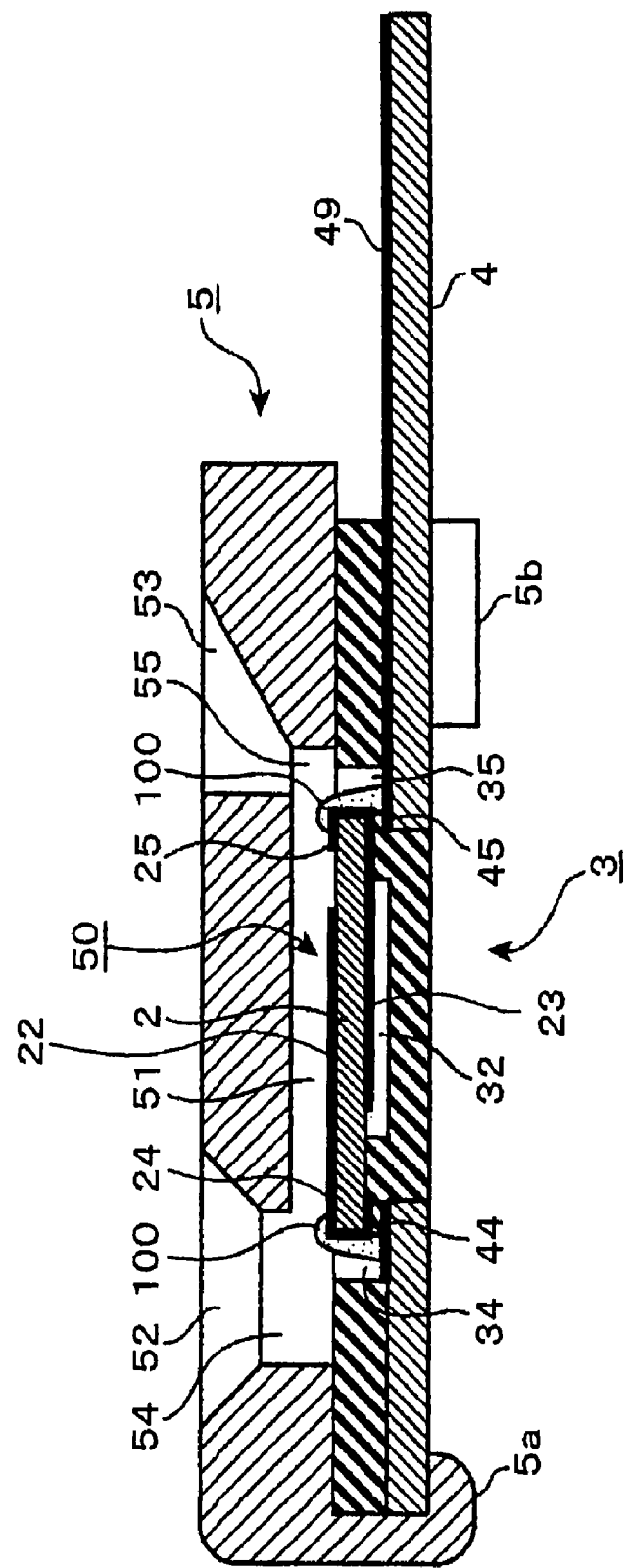
FIG. 4 is a vertical cross section of the quartz sensor.

The structure of the lid 5 will be explained next. The lid 5 has a recess 50 formed on the back surface side as shown in FIG. 3. The recess 50 includes a first area 51 having a space enclosing the whole of the recess 32 in the quartz holding member 3, a second area 54 and a third area 55 respectively formed both in front and in the rear of the first area 51, as shown in FIG. 3 and FIG. 4. The first area 51 serves as a measurement area where the sample solution comes into contact with the excitation electrode 22 of the quartz resonator 2, and an opposing surface 57 having a size equal to or larger than the excitation electrode 22 of the quartz resonator 2 is arranged on the upper surface of the first area 51 so that the excitation electrode 22 is to be housed within the projection area in the opposing surface 57. The second area 54 and the third area 55 respectively extend above the holes 34 and 35 for applying a conductive adhesive in the quartz holding member 3, and an pouring opening 52 and a confirmation opening (detection opening) 53 for the sample solution are respectively formed on the upper surface side. The recess 50 including the first area 51, the second area 54 and the third area 55 corresponds to a pouring space, and the bottom surface of the peripheral portion surrounding the recess 50, in other words, the inside surface of the lid 5, serves as a pressing surface (close contact surface) which comes in close contact with a surface surrounding the quartz resonator 2 in the quartz holding member 3 and presses it. A rib 56 is provided in the inside surface of the lid 5 so as to surround the pressing surface.

The pouring opening 52 is formed in a manner that the bore diameter thereof is increasing gradually from inside of the lid 5 to the upper surface of the lid 5, in other words, the inside of the pouring opening 52 is formed in a slope, for the purpose of pouring of the sample solution easier. The confirmation opening 53 is formed to have a slope portion milder in inclination than the slope of the confirmation opening 53 from inside of the lid 5 toward the rear end side of the upper surface of the lid 5 so that the water level appeared in the confirmation opening 53 is easy to be observed. Note that the confirmation opening 53 is formed so that the slope portion is exposed when the lid 5 is seen from the upper surface.

The quartz sensor having such a structure like this is assembled as follows. As described previously, the quartz holding member 3 is fitted into the circuit board 4, and the quartz resonator 2 is installed on the recess 31 of the quartz holding member 3 so that the quartz resonator 2 is fitted in the recess 31. Then, a conductive adhesive 100 is supplied from above the quartz holding member 3 using a dispenser or the like so that the derivation electrode 24 (25) of the quartz resonator 2 and the electrode 44 (45) of the circuit board 4 are electrically connected to each other via the hole 34 (35). The quartz resonator 2 is firmly fixed on the quartz holding member 3 by the conductive adhesive 100. Thus, an airtight space (space in the recess 31) is formed on the bottom surface side of the quartz resonator 2, and the Langevin type quartz sensor is composed.

Next, the assembly of the circuit board 4 and the quartz holding member 3 is covered with the lid 5 from the upper surface thereof so as to fit respective claws 5a, 5b and 5c into respective notch portions 4a, 4b and 4c, and is pressed toward the substrate. Then, the respective claws Sa, 5b and 5c formed on the lid 5 are bent toward the outside of the circuit board 4, and further the respective claws 5a, 5b and 5c come around the bottom surface of the peripheral portion of the circuit board 4 via the respective notch portions 4a, 4b and 4c. At the same time, the respective claws 5a, 5b and 5c are restored to their original shapes owing to the restoring force toward inside, so that the circuit board 4 is locked together by being caught with the respective claws 5a, 5b and 5c. The above-described pressing surface inside the lid 5 comes in close contact with the upper surface of the quartz holding member 3 to form the pouring space for the sample solution. In order to prevent impurities coming from the pouring opening 52 and the confirmation opening 53 from sticking to the quarts resonator 2 before measurement, the pouring opening 52 and the confirmation opening 53 are covered with a protective sheet in a film (not shown).

When the quartz sensor in the present embodiment is used, a predetermined quantity of the sample solution is poured into the second area 54 using an injector via the pouring opening 52 of the lid 5 by an operator, and a surface of the quartz resonator 2 comes in contact with a measurement medium by further pouring of the sample solution into the first area 51. At this time, blocked by a rib 56 stuck in the quartz holding member 3 on the lid 5, leakage of the sample solution from a gap between the lid 5 and the quartz holding member 3 into the outside of the quartz sensor is prevented with further reliability.

As described above, the quartz sensor in the present embodiment is easy in assembling, and since a large stress is not applied on the quartz resonator 2, it is possible to prevent damage to the quartz piece 21 at the time of manufacturing or using the quartz sensor. In addition, as described above, when the measurement frequency is intend to be high to enhance the measurement sensitivity, the quartz piece 21 needs to be thin, which makes the measurement largely affected even with a slight stress. The quartz resonator 2 is fixed to the rubber quartz holding member 3, and is not directly in contact with the circuit board 4, the stress applied on the quartz piece 21 is small, which makes it possible to conduct measurement with high sensitivity and accuracy. In the above-described embodiment, since the hole 43 is formed in the circuit board 4 and the projection 33 projecting toward the back surface side of the recess 31 of the quartz holding member 3 is fitted in the hole 43, the height of an airtight space (the space formed by the recess 32) being in contact with an excitation electrode of the quartz resonator 2 can be absorbed with the thickness of the circuit board 4, so that the thickness of the quartz holding member 3 can be made small. It is also possible, however, to make a structure to stack the back surface of the quartz holding member 3 with the front surface of the circuit board 4 without providing the hole 43 in the circuit board 4 so as to form the above-described airtight space by utilizing the thickness of the quartz holding member 3. In this event, the bottom of the airtight space corresponds to the front surface of the circuit board 4.

The sample solution poured from the pouring opening 55 flows also in the third pouring area 55 through the second pouring area 54 and the first pouring area 51, and the liquid level of the sample solution in the third pouring area 55 goes up. The liquid level of the sample solution arrives at the confirmation opening 53, and goes up continuously along the slope formed in the confirmation opening 53. Thereby, it becomes possible to easily confirm that the sample solution has been poured in the quartz sensor from outside of the quartz sensor. When the sample solution is not enough, since the quartz resonator 2 receives the influence of the surface tension of the sample solution, such a structure is effective. Furthermore, since it is possible to control the sample solution to be poured not to be excessive, it can give a convenience to the measurement. It is also possible to prevent the amount of supply of the sample solution to get excessive by observing the manner of liquid level increase. The quartz sensor may be scraped after using the measurement as it is, it may be reused by separating the lid 5 from the circuit board 4 by bending each claw of the lid 5 toward outside of the quartz sensor, and cleaning each part.

Figure 5:
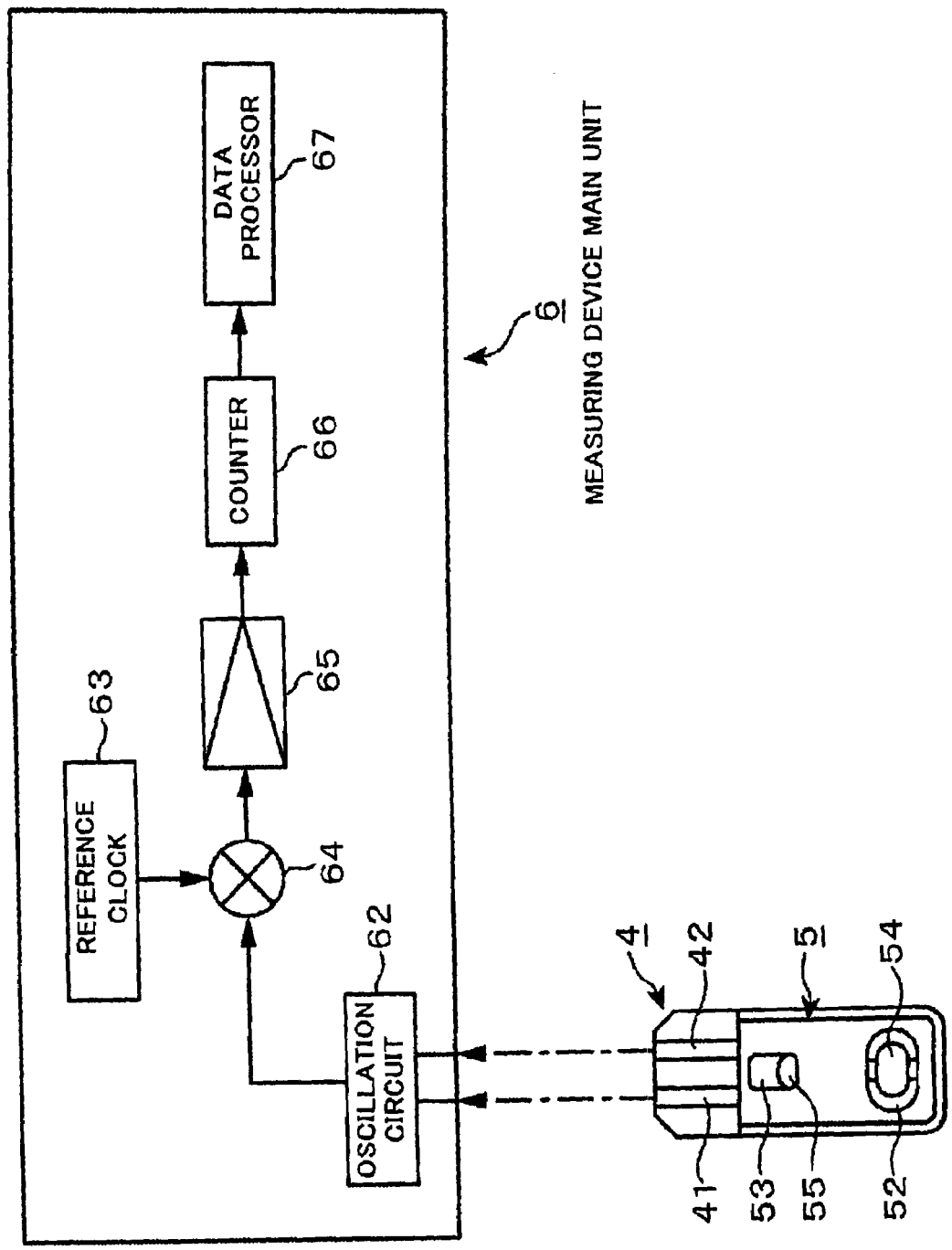
FIG. 5 is a block diagram showing a structural example of a measuring device main unit to which the quartz sensor relating to the present invention is connected.

Here, the quartz sensor is used as a sensor of a sensing device by connecting to a measuring device main unit 6 having a structure shown by, for instance, a block diagram FIG. 5. 62 in the drawing is an oscillation circuit for oscillating the quartz piece 21 of the quartz sensor, 63 is a reference clock generator for generating a reference frequency signal, 64 is a frequency difference detector composed of, for instance, a heterodyne wave detector and captures a frequency signal corresponding to the frequency difference between the oscillation circuit 62 and the reference clock generator 63 based on the frequency signal from the oscillation circuit 62 and the clock signal from the reference clock generator 63, 65 is an amplifier, 66 is a counter for counting the frequency of an output signal from the amplifier 65, 67 is a data processor.

For instance, 9 MHz is selected as the frequency of the quartz sensor, and 10 MHz is selected as the frequency of the reference clock generator 53. When an object to be detected, for instance, dioxin, is not adsorbed to the quartz resonator 2 held in the quartz sensor, the frequency difference detector 64 outputs the frequency signal (frequency difference signal) of 1 MHz, that is the difference between the frequency from the quartz sensor and the frequency from the reference clock, but when the object to be detected (for instance, dioxin) contained in the sample solution is adsorbed to the quartz resonator 2, since the natural frequency varies and the frequency difference signal varies on this account, the count value also varies at the counter 66. Then, the concentration or presence/absence of the object to be measured can be detected by preparing in advance a calibration curve on variation of frequency (variation of count value) and concentration of the object to be measured (for instance, dioxin) in the sample solution.

Figure 6A:
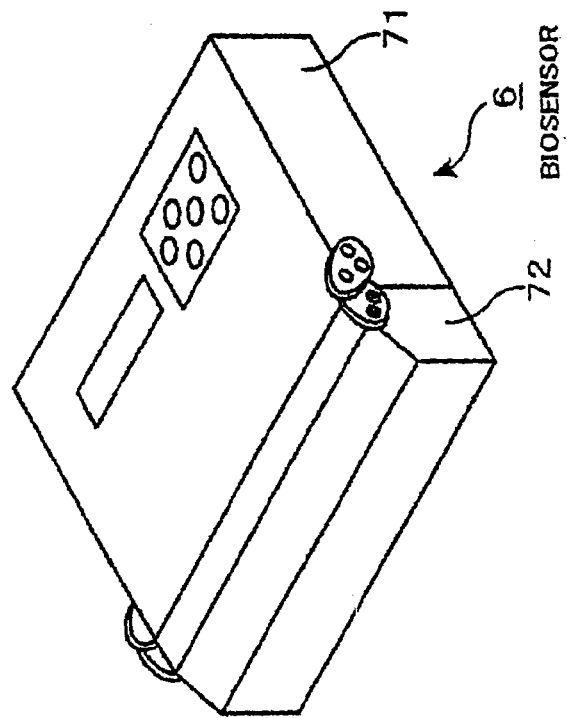
FIGS. 6A and 6B are perspective views showing a biosensor which is one example of the measuring device main unit.
Figure 6B:
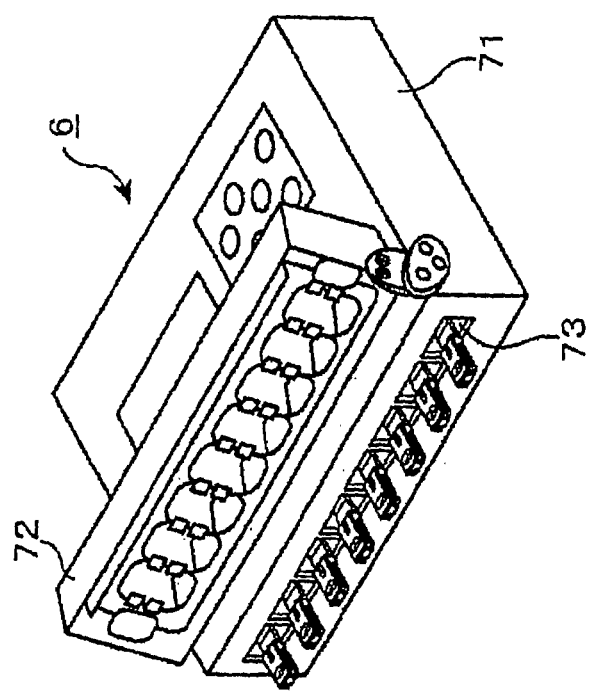

FIGS. 6A and 6B are views showing an example of the above-described measuring device main unit 6. As shown in FIG. 6A, the measuring device main unit 6 includes a main unit 71 and a retractable lid 72 formed in front of the main unit 71. When the lid 72 is opened, the front surface of the main unit 71 is appeared as shown in FIG. 6B. A plurality of plugs 73 of the quartz sensor is provided in front of the main unit 71, and the plural plugs 73 (for instance, 8 plugs) are formed in a straight line at fixed intervals.

The connecting terminal units 41 and 42 of the circuit board 4 and electrodes formed in the plugs 73 are electrically connected by horizontally inserting the rear end side of the circuit board 40 of the respective quartz sensors into the respective plugs 73 of the measuring device main unit 6 till s the predetermined depth, and at the same time, the quartz sensors are firmly fixed to the measuring device main unit 6 while the quartz sensors are kept horizontally by sandwiching the circuit board 4 by the insides of the plugs 73. Since this structure makes it possible to directly connect it to the measuring device main unit 6 without using a special attachment, the wiring is not routed around on the measurement table, so that the measurement work is easily performed.

Figure 7A:
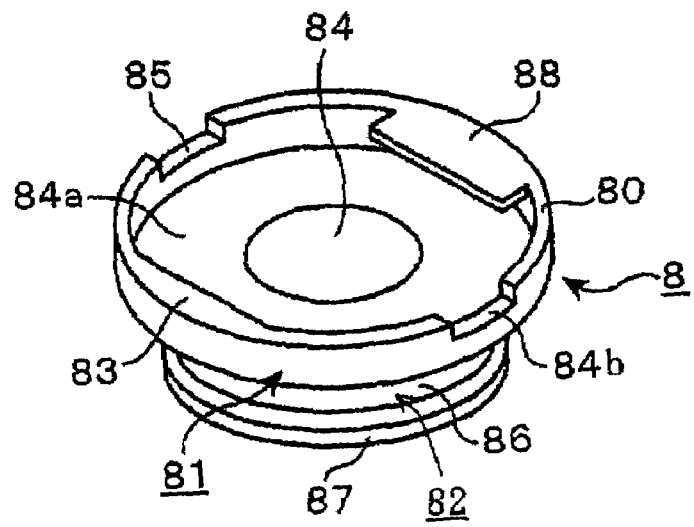
FIGS. 7A, 7B and 7C are explanatory views showing an example of a ring-shaped quartz holding member used in the quartz sensor relating to another embodiment.
Figure 7B:
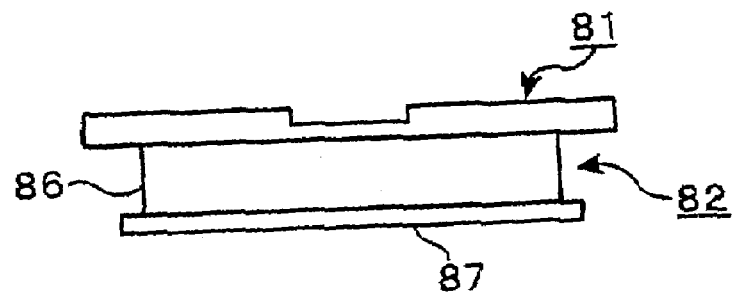
Figure 7C:
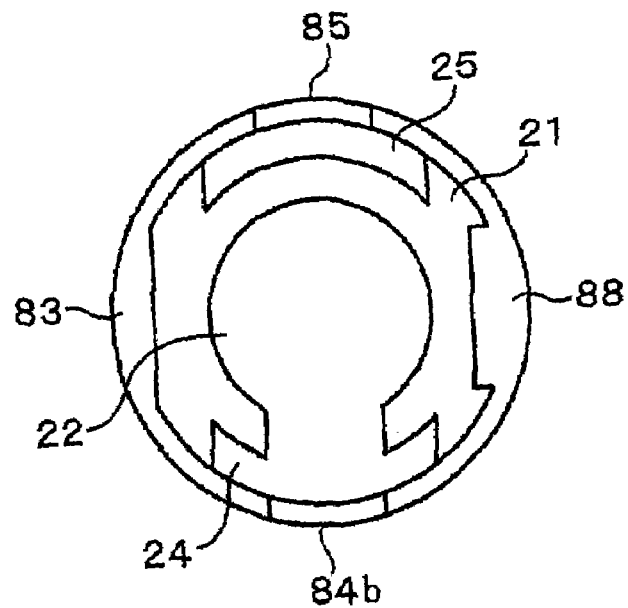
Figure 8A:
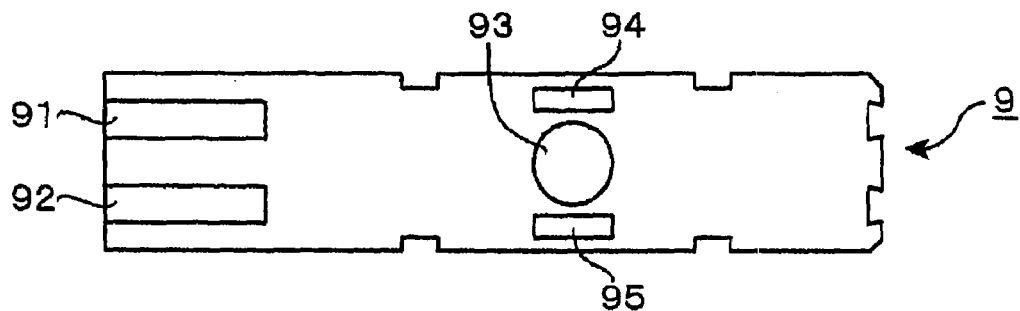
FIGS. 8A, 8B, 8C and 8D are assembly flow charts of the quartz sensor using the quartz holding member.
Figure 8B:
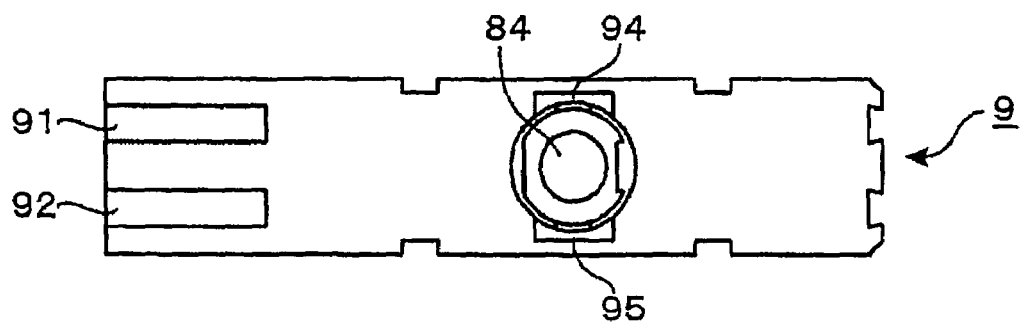

Another embodiment of the present invention will be explained next. FIGS. 7A, 7B and 7C show the ring-shaped quartz holding member 8 used in the quartz sensor relating to the present embodiment. The quartz holding member 8 is made of an elastic material such as rubber, and composed of a table 81 on one side for placing the quartz resonator and a fitting portion 82 on the other side for being fitted into the substrate 9. The table 81 has a through hole 84 formed in the center, having the same size as or a little larger than the excitation electrode 22 of the quartz resonator 2. The table 81 also includes a ring-shaped table surface 84a of which external size is nearly the same as the quartz resonator 2, and a peripheral wall 80 surrounding the periphery of this 84a. On the upper surface of the peripheral wall 80, notches 84b and 85 are formed at the positions facing each other. Between the notches 84b and 85 on the upper surface, a projected piece 88 projecting inward is formed via a gap from the table surface 84a corresponding to the thickness of the quartz piece 21. The internal surface facing the projected piece 88 in the peripheral wall 80 is formed straight so as to match with a straight portion in a portion of the periphery of the quartz piece 21. The fitting portion 82 is arranged in the center on the opposite side to the table surface 84a in the table 81, and formed to have an outer dimension able to be inserted into a through hole 93 (refer to FIG. 8A) which is a hole of the circuit board (for instance, a printed circuit board) 9 which will be described later. The fitting portion 82 also includes: a ring 86 with a length corresponding to the thickness of the circuit board 9; and a flange 87 formed on the top periphery of the ring 86. The inside space of the ring 86 is connected to the through hole 84.

Figure 8C:
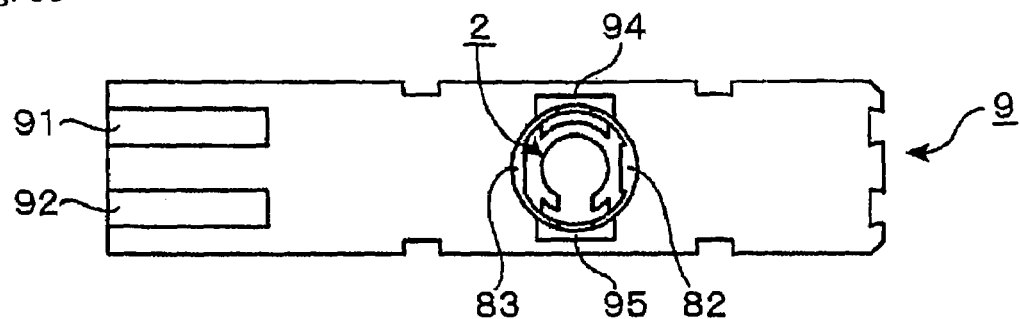
Figure 8D:
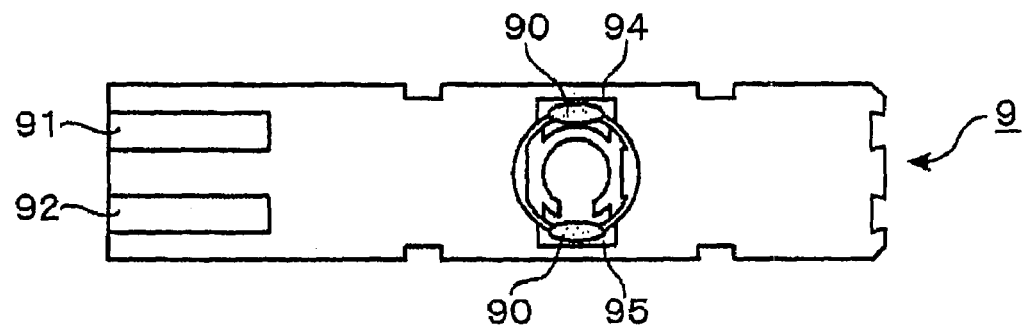

FIGS. 8A, 8B, 8C and 8D show a circuit board 9 used in the present embodiment and the assembly process thereof. The circuit board 9 is provided with connecting terminals 91 and 92 composed of a printed circuit on one end side. These connecting terminals 91 and 92 are detachable from the measuring device main unit 6 similarly to the previous embodiment. In the center of the circuit board 9, a round through hole 93 in a size corresponding to the outside shape of the ring 86 of the quartz holding member 8 is drilled, the flange 87 is engaged with the other surface side of the circuit board 9 by inserting the ring portion 86 into the through hole 93 from one surface side of the circuit board, so that the quartz holding member 8 is fixed to the circuit board 9. Thereafter, the quartz resonator 2 is fitted into the table 81 by lifting slightly the projected piece 82 of the table 81. FIG. 7C and FIG. 8C are plan views showing a state that the quartz resonator 2 is fitted into the table 81.

Figure 9A:
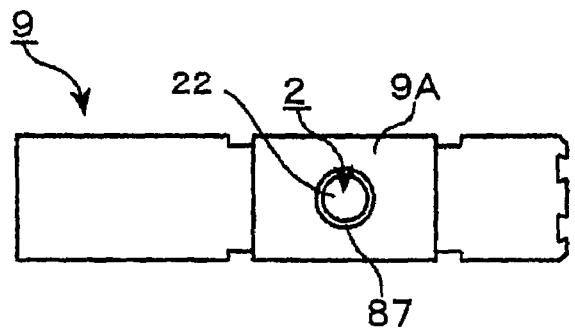
FIGS. 9A, 9B, 9C and 9D are assembly flow charts of the quartz sensor using the quartz holding member.
Figure 9B:
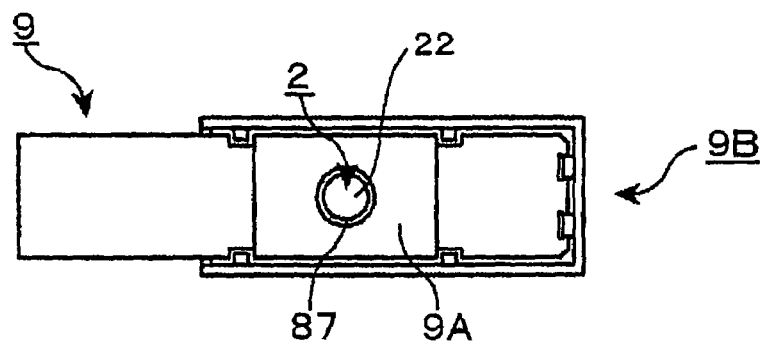
Figure 9C:
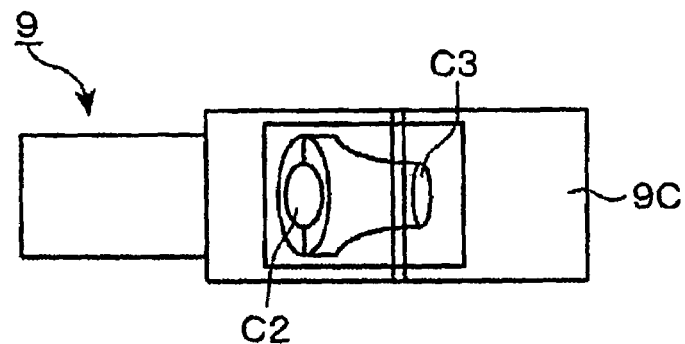
Figure 9D:
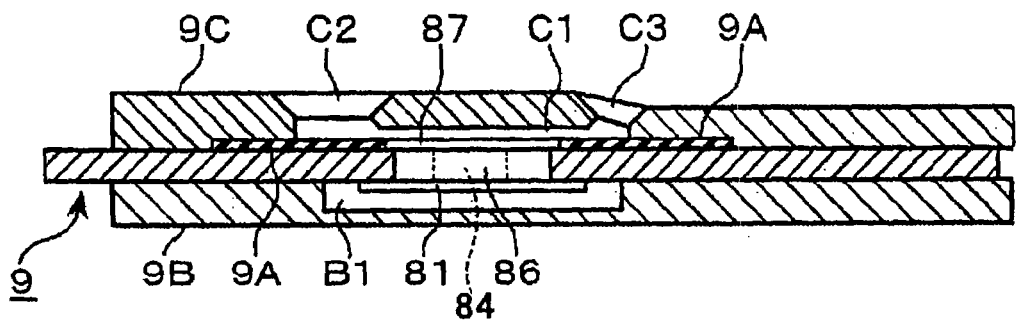
Figure 10:
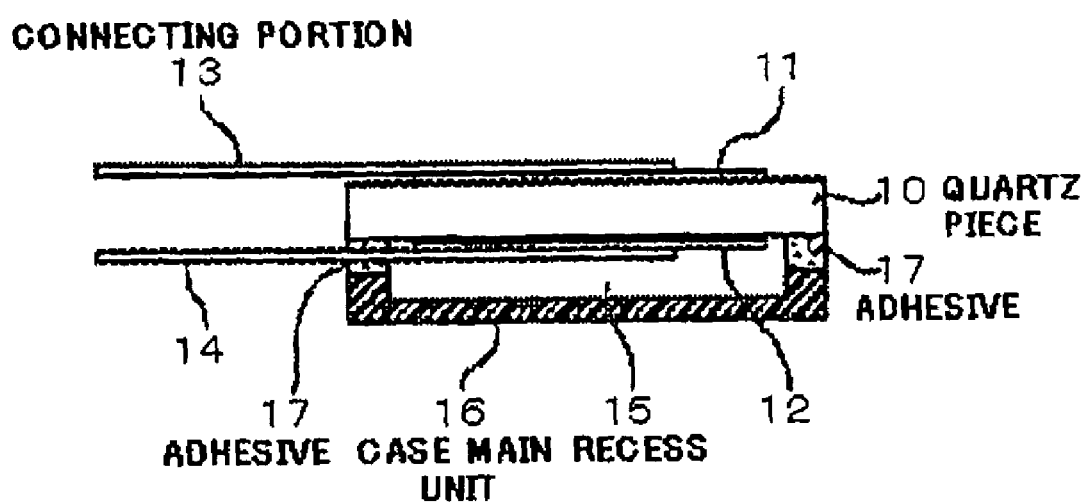
FIG. 10 is an explanatory view showing a structural example of a conventional quartz sensor.

Furthermore, electrodes (the derivation electrodes 24 and 25 in this embodiment) of the quartz resonator 2 and electrodes 94 and 95 of the circuit board 9 are connected by a conductive adhesive 90 via the notches 84b and 85 respectively. The electrodes 94 and 95 are electrically connected to the connecting terminals 91 and 92 respectively. Then, as shown in FIG. 9A, an elastic sheet, for instance, a rubber sheet 9A is overlaid on the other side of the circuit board 9 so that the through hole 93 formed in the center thereof and the quartz resonator 2 are put on top of each other, and an upper case 9C serving as a lid is further put on this sheet 9A so that the periphery of the upper case 9C is engaged with the periphery of the circuit board 9 (FIG. 9C). A pouring space C1, and a pouring opening C2, a confirmation opening C3 connecting to this pouring space are formed on the upper case 9C as in the previous embodiment. A lower case 9B serving as a base support is mounted on one surface side of the circuit board 9 (FIG. 9B). A recess B1 is formed at a position corresponding to the table 81 in the lower case 9B as shown in FIG. 9D, and a space in the recess B1 forms an airtight space coming into contact with one surface side of the quartz resonator 2. Accordingly, a Langevin type quartz sensor is structured also in this embodiment.

The quartz sensor assembled in this way has a structure that the one surface side of the quartz resonator 2 comes into contact with the pouring space of a sample solution via the ring hole 84 of the quartz holding member 8, which makes it possible to conduct measurement similarly to the previous embodiment. Since the quartz resonator is equipped with the printed circuit board via the elastic quartz holding member in the embodiment, the assembly work is easy and the possibility of damage to the quartz resonator 2 is reduced.

The invention claimed is:

1. A quartz sensor used for detecting an object to be measured in a sample solution, comprising:

a circuit board equipped with a connecting terminal unit which is configured to connect to a measuring device main unit and electrodes electronically connected to the connecting terminal unit;

a quartz holding member holding made an elastic material provided with a recess for forming an airtight space, and stacked above said circuit board;

a quartz resonator formed of a quartz piece equipped with excitation electrodes which are arranged on one surface side and on another surface side of the quartz piece respectively and are electrically connected to the electrodes of said circuit board, and said quartz resonator being held by said quartz holding member in a state that the excitation electrode on the another surface side covers the recess so as to face said recess;

an adsorbing layer provided on the excitation electrode on said one surface side, and said adsorbing layer having a capacity for adsorbing the object to he measured in the sample solution;

a lid closely contacting with a periphery of said recess in said quartz holding member, and forming a pouring space for the sample solution by enclosing an upper space on said one surface side of said quartz resonator;

said lid including an outer surface defining a pouring opening for the sample solution and a confirmation opening for confirming that the sample solution is poured into the pouring space, wherein said pouring opening and said confirmation opening are connected in an inside or the lid to said pouring space, and a conductive adhesive connecting the excitation electrode of said quartz resonator and the electrode of said circuit board, wherein a natural frequency of the quartz resonator varies by adsorption of the object to he measured on said adsorbing layer.

2. The quartz sensor according to claim 1, wherein said quartz holding member is provided with a hole for the conductive adhesive at a position corresponding to at least one of said excitation electrodes, and the at least one of the excitation electrodes and at least one of the electrodes of the circuit board are connected by the conductive adhesive via the hole.

3. The quartz sensor according to claim 1, wherein the recess of the quartz holding member holds said quartz resonator and has a bottom wall, the circuit board defines a hole for the quartz holding member and a bottom side of the bottom wall of the recess for the quartz holding member is fitted into the hole of the circuit board.

4. The quartz sensor according to claim 1, wherein a claw is formed on a periphery of said lid, and a notch is formed in said circuit board, so that the lid is lined on the circuit board by locking the claw, due to restoration force of said claw, inside the notch.

5. A quartz sensor used for detecting an object to be measured in a sample solution, comprising:

a circuit board provided with a connecting terminal unit which is configured to connect to a measuring device main unit electrodes electrically connected to the connecting terminal unit and a hole;

a ring-shaped quartz holding member fitted into said hole and made of an elastic material;

a quartz resonator formed of a quartz piece equipped with excitation electrodes which are arranged on one surface side and on another surface side of the quartz piece respectively and electrically connected to the electrodes of said circuit board, and held by the ring-shaped quartz holding member so as to cover at least a portion of a first side of said ring-shaped quartz holding member disposed adjacent one surface side of said circuit board;

an adsorbing layer provided on the excitation electrode on said one surface side, and said adsorbing layer having a capacity for adsorbing the object to be measured in the sample solution;

a base support structured to form an airtight space on another surface side of said quartz resonator for covering one surface side of the circuit board;

a lid closely contacting with periphery of a ring hole in said quartz holding member, and forming a pouring space for the sample solution by enclosing an upper space on the other surface side of the quartz resonator so as to cover surface side of the circuit board;

said lid including an outer surface defining a pouring opening for the sample solution and a confirmation opening for confirming that the sample solution is pouring into the pouring space, wherein said pouring opening and said confirmation opening are connected in an inside of the lid to said pouring space; and a conductive adhesive for bonding die excitation electrodes of said quartz resonator to the electrodes of said circuit board, wherein the natural frequency of the quartz resonator varies by adsorption of to object to be measured on the adsorbing layer.

6. The quartz sensor according to claim 1 or claim 2, wherein said quartz holding member is made of rubber.

7. The quartz sensor according to claim 1 or claim 2, wherein the circuit board can be inserted into and removed from the measuring device main unit, and when the circuit board is inserted, the connecting terminal unit is connected to the measuring device main unit.

8. A sensing device, comprising:

a quartz sensor according to any one of claim 1 to claim 2; and a measuring device main unit for detecting the variation of the natural frequency of a quartz resonator and detecting the object to be measured in the sample solution based on the detection result.

9. A sensing device, comprising:

a quartz sensor according to claim 6; and a measuring device main unit for detecting the variation of the natural frequency of a quartz resonator and detecting the object to be measured in the sample solution based on the detection result.

10. A sensing device, comprising:

a quartz sensor according to claim 7; and a measuring device main unit for detecting the variation of the natural frequency of a quartz resonator and detecting the object to be measured in the sample solution based on the detection result.

11. A quartz sensor used for detecting an object to be measured in a sample solution, comprising:

a circuit board having a connecting terminal unit which is configured to connect to a measuring device main unit, and electrodes electrically connected to the connecting terminal with, said circuit board, defining a recess;

a quartz resonator formed of a quartz piece having excitation electrodes which are arranged on one surface side and on another surface side of the quartz piece respectively and are electrically connected to the electrodes of said circuit board, and said quartz resonator being held in a state that the excitation electrode on the another surface side is disposed aligned with the recess;

an adsorbing layer provided on the excitation electrode on said one surface side, and said adsorbing layer having a capacity for adsorbing the object to be measured in the sample solution;

a lid forming a pouring space for the sample solution by enclosing an upper space communicating to said one surface side of said quartz resonator;

said lid including an outer surface defining a pouring opening for the sample solution and a confirmation opening for confirming that the sample solution is poured into the pouring space, wherein said pouring opening and said confirmation opening are connected in an inside of the lid to said pouring space;

a conductive adhesive connecting the excitation electrode of said quartz resonator and the electrode of said circuit board;

said quartz resonator having a natural frequency that varies by adsorption of the object to be measured on said adsorbing layer.

12. A sensing device, comprising:

a quartz sensor according to claim 11; and a measuring device main unit for detecting the variation of the natural frequency of a quartz resonator and detecting the object to be measured in the sample solution based on the detection result.

* * * * *